United States Patent
Fischvogt et al.

(10) Patent No.: US 10,022,148 B2
(45) Date of Patent: Jul. 17, 2018

(54) TWO-SHOT MOLDED OPTICAL OBTURATOR

(71) Applicant: Covidien LP, Mansfield, MA (US)

(72) Inventors: Gregory Fischvogt, Denver, CO (US); Danny Berry, Cheshire, CT (US); Emily Davis, Cheshire, CT (US); Norvin Asido, Southington, CT (US)

(73) Assignee: Covidien LP, Mansfield, MA (US)

( * ) Notice: Subject to any disclaimer, the term of this patent is extended or adjusted under 35 U.S.C. 154(b) by 419 days.

(21) Appl. No.: 14/650,474

(22) PCT Filed: Dec. 20, 2013

(86) PCT No.: PCT/US2013/076767
§ 371 (c)(1),
(2) Date: Jun. 8, 2015

(87) PCT Pub. No.: WO2014/105661
PCT Pub. Date: Jul. 3, 2014

(65) Prior Publication Data
US 2015/0313631 A1    Nov. 5, 2015

Related U.S. Application Data

(60) Provisional application No. 61/746,269, filed on Dec. 27, 2012.

(51) Int. Cl.
*A61B 1/313* (2006.01)
*A61B 17/34* (2006.01)
(Continued)

(52) U.S. Cl.
CPC .......... *A61B 17/3417* (2013.01); *A61B 1/313* (2013.01); *A61B 90/37* (2016.02);
(Continued)

(58) Field of Classification Search
CPC ................. A61B 1/313; B29C 2045/0089
(Continued)

(56) References Cited

U.S. PATENT DOCUMENTS 6,887,417 B1    5/2005  Gawreluk et al.
7,470,230 B2   12/2008  Smith et al.
(Continued)

FOREIGN PATENT DOCUMENTS

CN    2262429 Y    9/1997
EP    2471569 A1   7/2012
(Continued)

OTHER PUBLICATIONS

International Search Report for (PCT/US2013/076767) date of completion is Apr. 28, 2014 (4 pages).
(Continued)

*Primary Examiner* — Elizabeth A Burkhart (57) ABSTRACT

A method of manufacturing an optical obturator includes providing an injection mold including a mold cavity defining an outer surface of the optical obturator and a core pin centrally positioned within the mold cavity. The core pin defines an inner surface of the optical obturator. In particular, the core pin may be cantilevered to the injection mold. The method further includes injecting a first material between the core pin and the mold cavity to form the tubular shaft and injecting a second material between a distal portion of the core pin and a distal portion of the mold cavity to form the optical tip.

11 Claims, 11 Drawing Sheets

(51) Int. Cl.

| | |
|---|---|
| *B29C 45/16* | (2006.01) |
| *B29C 45/26* | (2006.01) |
| *B29C 45/36* | (2006.01) |
| *A61B 90/00* | (2016.01) |
| *B29K 69/00* | (2006.01) |
| *B29L 31/00* | (2006.01) |
| *A61B 17/00* | (2006.01) |

(52) U.S. Cl.
CPC .......... *B29C 45/16* (2013.01); *B29C 45/1639* (2013.01); *B29C 45/26* (2013.01); *B29C 45/261* (2013.01); *B29C 45/36* (2013.01); *A61B 2017/00526* (2013.01); *A61B 2017/00907* (2013.01); *A61B 2017/3454* (2013.01); *B29C 2045/363* (2013.01); *B29K 2069/00* (2013.01); *B29K 2995/0026* (2013.01); *B29L 2031/7546* (2013.01); *F04C 2270/041* (2013.01)

(58) Field of Classification Search
USPC .............................................. 264/31–34, 478
See application file for complete search history.

(56) References Cited

U.S. PATENT DOCUMENTS

| | | |
|---|---|---|
| 7,794,644 B2 | 9/2010 | Taylor et al. |
| 8,821,526 B2 | 9/2014 | Winfree et al. |
| 9,084,867 B2 | 7/2015 | Triel et al. |
| 9,101,315 B2 | 8/2015 | Winfree et al. |
| 2005/0033237 A1 | 2/2005 | Fentress et al. |
| 2005/0288622 A1 | 12/2005 | Albrecht et al. |
| 2006/0106287 A1 | 5/2006 | Webler et al. |
| 2007/0075465 A1* | 4/2007 | Taylor ................ A61B 17/3417 264/512 |
| 2008/0027414 A1 | 1/2008 | Tanghoj et al. |
| 2009/0093833 A1 | 4/2009 | Smith |
| 2009/0093835 A1 | 4/2009 | Heinrich et al. |
| 2009/0306697 A1 | 12/2009 | Fischvogt |
| 2009/0308184 A1* | 12/2009 | Blekher ............... A61B 5/1411 73/864.63 |
| 2010/0016664 A1 | 1/2010 | Viola |
| 2010/0100045 A1* | 4/2010 | Pravongviengkham A61B 17/3421 604/164.09 |
| 2011/0004061 A1 | 1/2011 | Smith |
| 2011/0213343 A1 | 9/2011 | Tanghoj et al. |
| 2011/0254202 A1 | 10/2011 | Aeschlimann |
| 2012/0150130 A1* | 6/2012 | Triel ................ A61M 25/0015 604/264 |
| 2013/0310773 A1 | 11/2013 | Richard et al. |

FOREIGN PATENT DOCUMENTS

| | | |
|---|---|---|
| JP | 2007-260218 | 10/2007 |
| KR | 10-2006-0105596 | 10/2006 |
| WO | 2005/032348 A2 | 4/2005 |
| WO | 2008/064344 A2 | 5/2008 |
| WO | 2014105661 A1 | 7/2014 |

OTHER PUBLICATIONS

European Search Report issued in corresponding European Appln. No. EP 13869818 dated Aug. 8, 2016.
Chinese Office Action issued in corresponding Chinese Application No. 201380068575.0 dated Jul. 6, 2016.
CN1602214, U.S. Pat. No. 6,887,417.
CN102264524, U.S. Publication No. 2011/0254202.
CN102802714, U.S. Pat. No. 9,084,867.

* cited by examiner

FIG. 16

TWO-SHOT MOLDED OPTICAL OBTURATOR

CROSS-REFERENCE TO RELATED APPLICATION

This application is a National Stage Application of PCT/US2013/076767 under 35 USC § 371 (a), filed Dec. 20, 2013, which claims priority to and the benefit of U.S. Provisional Patent Application Ser. No. 61/746,269, filed on Dec. 27, 2012, the entire contents of which are incorporated by reference herein.

TECHNICAL FIELD

The present disclosure relates to an optical obturator for tunneling through body tissue and, more particularly, to a two-shot molded optical obturator and a method of manufacture thereof.

BACKGROUND OF RELATED ART

Endoscopic and laparoscopic minimally invasive procedures have been used for introducing medical devices into a patient and for viewing portions of the patient's anatomy. Typically, to view a desired anatomical site, a clinician inserts an endoscope inside the patient to render images of the anatomical site. In endoscopic surgical procedures, surgery is performed in any hollow organ or tissue of the body through a small incision or through narrow endoscopic tubes (cannulas) inserted through a small entrance wound in the skin. In laparoscopic procedures, surgical operations in the abdomen are performed through small incisions (usually about 0.5 cm to about 1.5 cm). Laparoscopic and endoscopic procedures often require the clinician to act on organs, tissues and vessels far removed from the incision, thereby requiring that any instruments used in such procedures be of sufficient size and length to permit remote operation.

Typically, a trocar is used to puncture the body cavity and includes a cannula, which remains in place for use during the laparoscopic procedure. Generally, a trocar includes a stylet or obturator for penetrating the body cavity.

Therefore, a need exists for a cost effective optical obturator that is also easy to manufacture.

SUMMARY

There is provided a method of manufacturing an optical obturator including a tubular shaft and an optical tip formed with the tubular shaft. In particular, the optical obturator defines a lumen configured and dimensioned to receive an optical instrument for receiving an image of tissue. The method includes providing an injection mold including a mold cavity defining an outer surface of the optical obturator and a core pin centrally positioned within the mold cavity and defining an inner surface of the optical obturator. The core pin may be cantilevered to the injection mold. The method further includes injecting a first material between the core pin and the mold cavity to form the tubular shaft and injecting a second material between a distal portion of the core pin and a distal portion of the mold cavity to form the optical tip.

In an embodiment, a distal end portion of the core pin is cantilevered to the injection mold.

In another embodiment, the method may further include detaching the core pin from the injection mold and translating the core pin within the tubular shaft prior to injecting the second material. Moreover, the method may further include detaching the core pin and positioning the core pin within the tubular shaft such that the core pin is centrally supported by the tubular shaft. Additionally, the method may further include curing the second material such that the second material encapsulates a distal portion of the tubular shaft.

In still another embodiment, injecting the second material may include injecting a high-flow polycarbonate material. The second material may be a transparent, molten polymeric material having high-flow properties such that the polymeric material flows between a surface of the mold cavity and the core pin.

In yet another embodiment, the core pin may be detachably supported with the injection mold.

In yet another embodiment, the optical tip may define a blunt end portion configured for separation of tissue planes and blunt dissection of cavity linings. In addition, the core pin may have a varying diameter.

In yet another embodiment, injecting the first material between the core pin and the mold cavity to form the tubular shaft may further include forming a latch assembly.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

Various embodiments of the optical obturator disclosed herein may be employed in endoscopic, laparoscopic, open surgical procedures, and interventional and intralumenal procedures such as GI sheathing (metabolic/bariatric) and/or banding. In addition, the optical obturator of the present disclosure may be utilized for post-operative monitoring, diagnostics and combinations thereof.

Various embodiments of the optical obturator of the present disclosure may be used with devices inserted in a patient to provide visualization of the target site. These devices may be introduced into the patient using minimally invasive procedures through natural orifices such as, e.g., navel, vagina and/or anus, or via a device inserted through a trocar, for example, and may be adapted to provide images of the surgical site or anatomic location such as the lungs, liver, stomach, gall bladder, urinary tract, reproductive tract, and intestinal tissue, for example. Once positioned at the target site, the surgical visualization devices provide images that enable the clinician to more accurately diagnose and provide more effective treatment of the diseased tissue. In embodiments, the visualization apparatus may be inserted into the tissue treatment region percutaneously. In other embodiments, the surgical visualization device may be introduced into the tissue treatment region endoscopically (e.g., laparoscopically and/or thoracoscopically), through small keyhole incisions via a trocar, or through a natural orifice.

Figures 1, 2, 3:
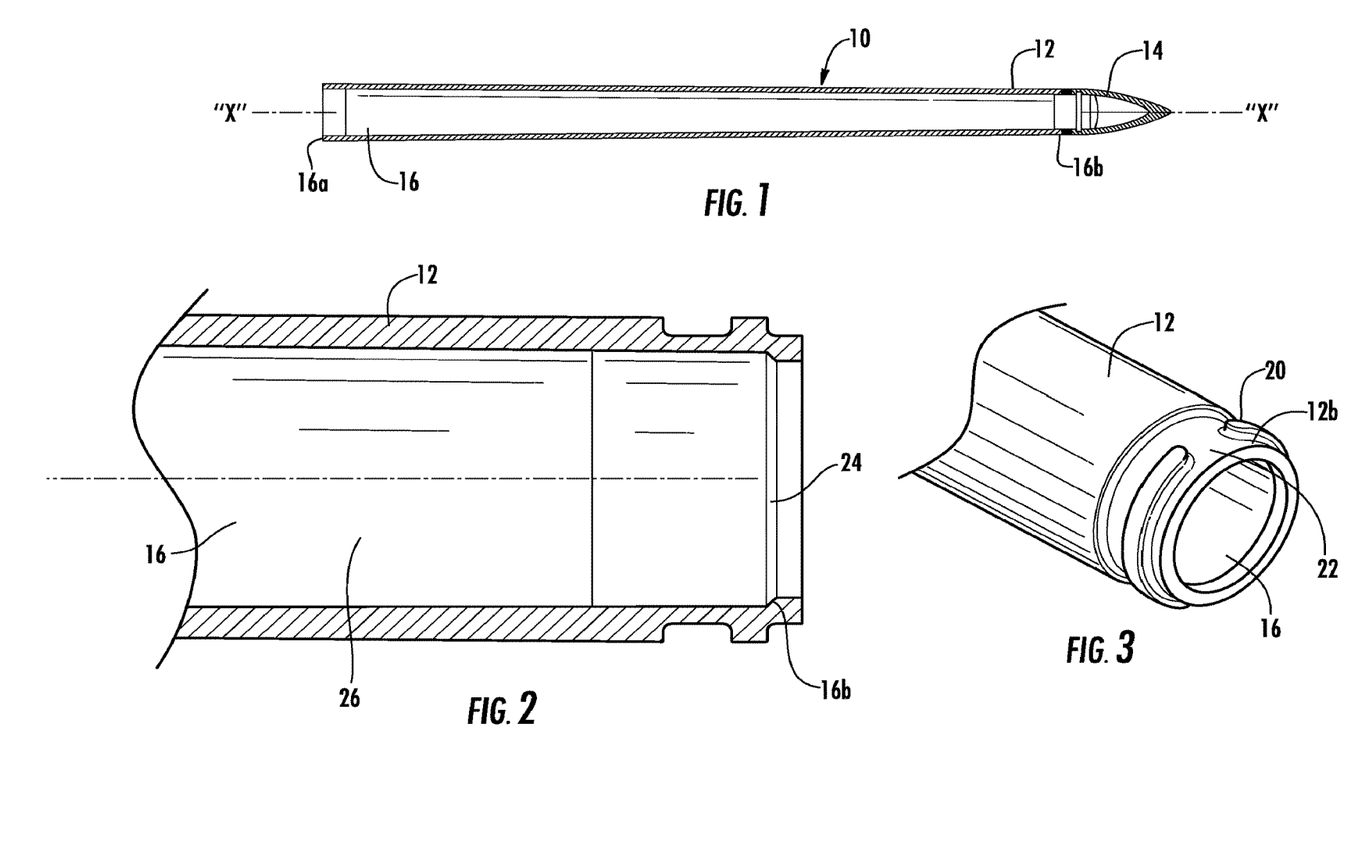
FIG. 1 is a longitudinal cross-sectional view of an optical obturator formed using a two-shot molding technique in accordance with an embodiment of the present disclosure.
FIG. 2 is a partial cross-sectional view of a distal end portion of a tubular shaft of the optical obturator of FIG. 1.
FIG. 3 is a partial perspective view of the distal end portion of the tubular shaft of the optical obturator of FIG. 1.

With reference now to FIG. 1, there is illustrated an optical obturator 10 formed by using a two-shot molding technique in accordance with an embodiment of the present disclosure. Optical obturator 10 is configured to penetrate tissue and permit visualization of tissue to the clinician performing the procedure. Optical obturator 10 includes a tubular shaft 12 and an over-molded optical tip portion 14 extending distally from tubular shaft 12. Optical tip portion 14 is formed with tubular shaft 12. Tubular shaft 12 is made from, e.g., molten polymer. Tubular shaft 12 is substantially hollow in structure to provide a working channel 16 configured and dimensioned to receive an endoscope therein. The endoscope may be any conventional scope suitable for endoscopic applications including, e.g., a laparoscope, arthroscope, colonoscope, etc. The endoscope may incorporate an optical train or lens arrangement which is capable of transmitting an image of an object from the distal or objective lens through an eyepiece or a monitor for viewing by the clinician.

In particular, working channel 16 is configured and dimensioned to receive the endoscope therein and to enable the endoscope to be positioned adjacent optical tip portion 14, which serves as a viewing area. The positioning of the endoscope adjacent optical tip portion 14 enables the clinician to visually observe body tissue as it is being separated by optical obturator 10, which, in turn, enables the clinician to avoid causing trauma to vessels or organs. A proximal end portion 16a of working channel 16 has a larger diameter than the diameter of a distal end portion 16b thereof. Such a configuration facilitates insertion and centering of the endoscope in working channel 16. Moreover, working channel 16 includes a smooth surface finish configured to facilitate sliding insertion and removal of the endoscope towards and away from optical tip portion 14.

With reference now to FIG. 2, distal end portion 16b of working channel 16 includes a shoulder 24 extending radially inward from an inner wall 26 of working channel 16. In particular, shoulder 24 defines a tapered/angled surface to facilitate centering of the endoscope with shoulder 24. Moreover, shoulder 24 serves as a stop for the endoscope. Such a configuration isolates any force that is applied on the endoscope to position the endoscope adjacent optical tip portion 14 of optical obturator 10. Specifically, the force is transmitted only to tubular shaft 12, e.g., shoulder 24, and not to the over-molded optical tip portion 14. This reduces the risk of inadvertent disengagement of the over-molded optical tip portion 14 from tubular shaft 12 during a surgical procedure.

While the diameter of working channel 16 varies along the length of tubular shaft 12, tubular shaft 12 has a wall having a substantially uniform thickness. In embodiments, the wall thicknesses of tubular shaft 12 may be from about 0.02 inches (about 0.5 mm) to about 0.025 inches (about 0.65 mm) for about a 5 mm to about 12 mm optical obturator.

With reference now to FIG. 3, a distal end portion 12b of tubular shaft 12 includes at least one axial retention rib 20 circumferentially disposed around distal end portion 12b of tubular shaft 12 and configured to inhibit axial movement or disengagement of optical tip portion 14. Distal end portion 12b of tubular shaft 12 further includes a flow channel 22 configured to enable the molding material of optical tip portion 14 to flow through flow channel 22 to facilitate distribution of the molten material therethrough during the over-molding process. In particular, flow channel 22 provides torsional retention of optical tip portion 14 relative to shaft 12, e.g., inhibits rotation of optical tip portion 14 relative to tubular shaft 12. The optical tip portion 14 is formed over or on an outer surface of distal end portion 12b of tubular shaft 12. In this manner, as the molten material of optical tip portion 14 cools, optical tip portion 14 shrinks onto distal end portion 12b of tubular shaft 12, and thereby strengthening the bond therebetween. Such a configuration provides a stronger bond compared to an optical tip portion that is molded onto, e.g., an inner surface, of tubular shaft 12.

Figure 4:
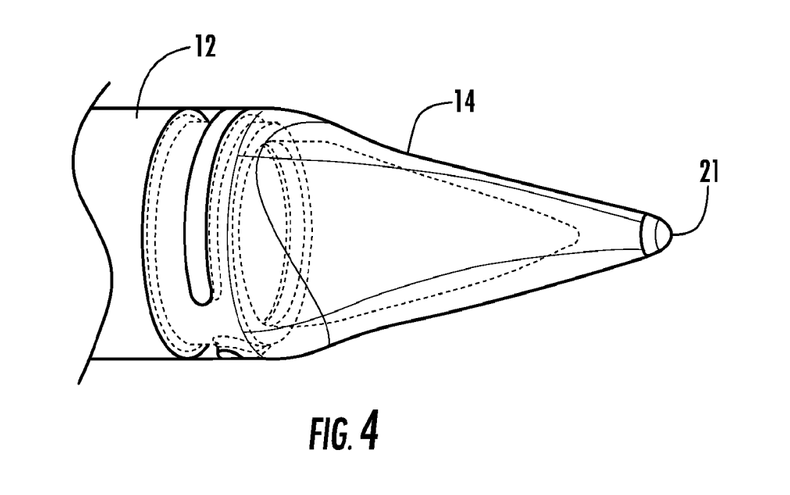
FIG. 4 is a partial perspective view of the optical obturator of FIG. 1.
Figure 5:
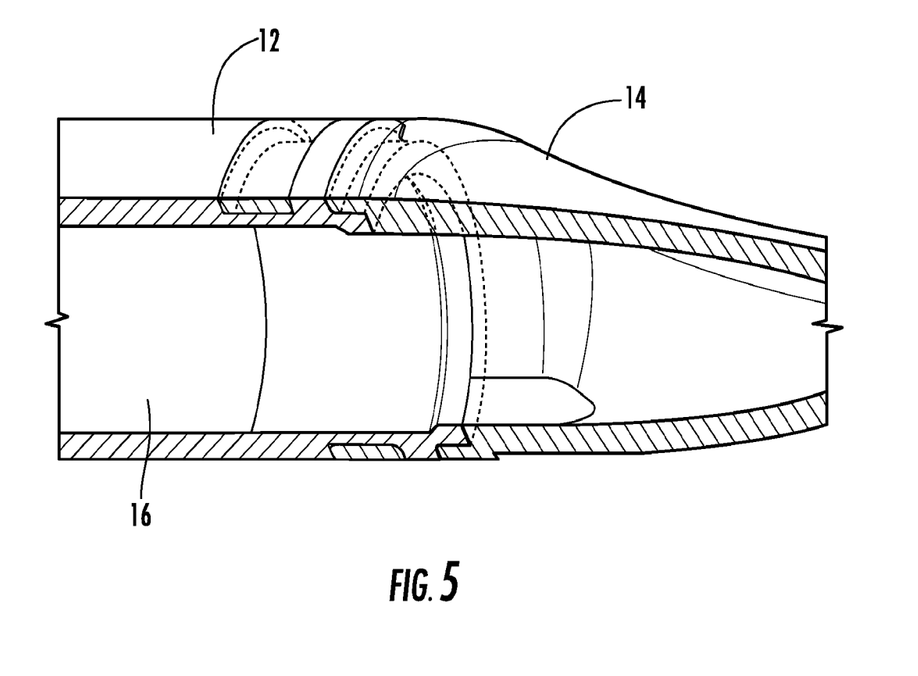
FIG. 5 is partial perspective view of the optical obturator of FIG. 1 with a cutaway portion illustrating a working channel of the optical obturator.

With reference to FIGS. 4 and 5, over-molded optical tip portion 14 defines a bladeless tip or a blunt end portion 21 for separating tissue planes and blunt dissection of cavity linings during a surgical procedure. Blunt end portion 21 permits initial insertion within an opening, e.g., a pre-cut scalpel incision, in tissue and facilitates advancement of tubular shaft 12 between the tissue layers to gently dissect tissue, without any further cutting or incising of tissue. After initial insertion and continued distal insertion, tubular shaft 12 continues to gently enlarge the opening in tissue. It is contemplated that other tip configurations including full radius or generally tapered shapes may be used. In addition, the tip may include sharp edges or molded blades.

Optical tip portion 14 is made of a transparent material to provide visualization of the tissue tract and the body cavity through the endoscope. Optical tip portion 14 may be constructed from a number of transparent materials such as, e.g., acrylic, glass, polystyrene, polycarbonate, or amorphous nylon.

In particular, interior and exterior surfaces of blunt end portion 21 are refracting surfaces that are adapted to direct light along a predetermined path, e.g., along a direction substantially parallel to a longitudinal axis "X-X" (FIG. 1). This arrangement provides for generally direct or forward viewing and illumination of the surgical site.

With reference to FIGS. 4 and 5, the thin-wall configuration of optical tip portion 14 enables light to travel through the material with reduced loss in intensity, and thereby enhancing the visibility of tissue therethrough as optical obturator 10 is advanced and placed into the targeted body cavity. The thin-wall configuration also reduces distortion of the image viewed through optical tip portion 14 and maintains the color accuracy of the viewed tissue.

With reference now to FIGS. 6-10, a method of forming optical obturator 10 using a two-shot molding technique in accordance with an embodiment of the present disclosure is described. In forming optical obturator 10 via two-shot injection molding, a high-flow material such as, e.g., polycarbonate material, may be used. For example, polycarbonate material is substantially transparent to enable visualization of a body wall and hollow cavity as optical obturator 10 is being placed into a patient. In forming optical obturator 10 via injection molding, a core pin 50 and an injection mold 500 defining a cavity 502 including outer dimensions of optical obturator 10 is utilized. Mold cavity 502 produces the outer surface dimensions and details of optical obturator 10. Core pin 50 produces the inner surface dimensions and details of optical obturator 10. Core pin 50 is positioned substantially in the center of mold cavity 502, whereby core pin 50 and mold cavity 502 are longitudinally aligned. In contrast to conventional injection molding that utilizes core pin supports (not shown) that support core pin 50 at various points on core pin 50, a distal end 50b of core pin 50 is cantilevered to injection mold 500, which, in turn, eliminates the need for the core pin supports. In particular, distal end 50b of core pin 50 is cantilevered to mold 500 by a clamp 555. In this manner, tubular shaft 12 includes hermetically sealed walls, e.g., walls without any bores formed by core pin supports. Thus, tubular shaft 12 inhibits introduction of tissue and fluids into working channel 16 through an outer surface of tubular shaft 12.

Figure 8:
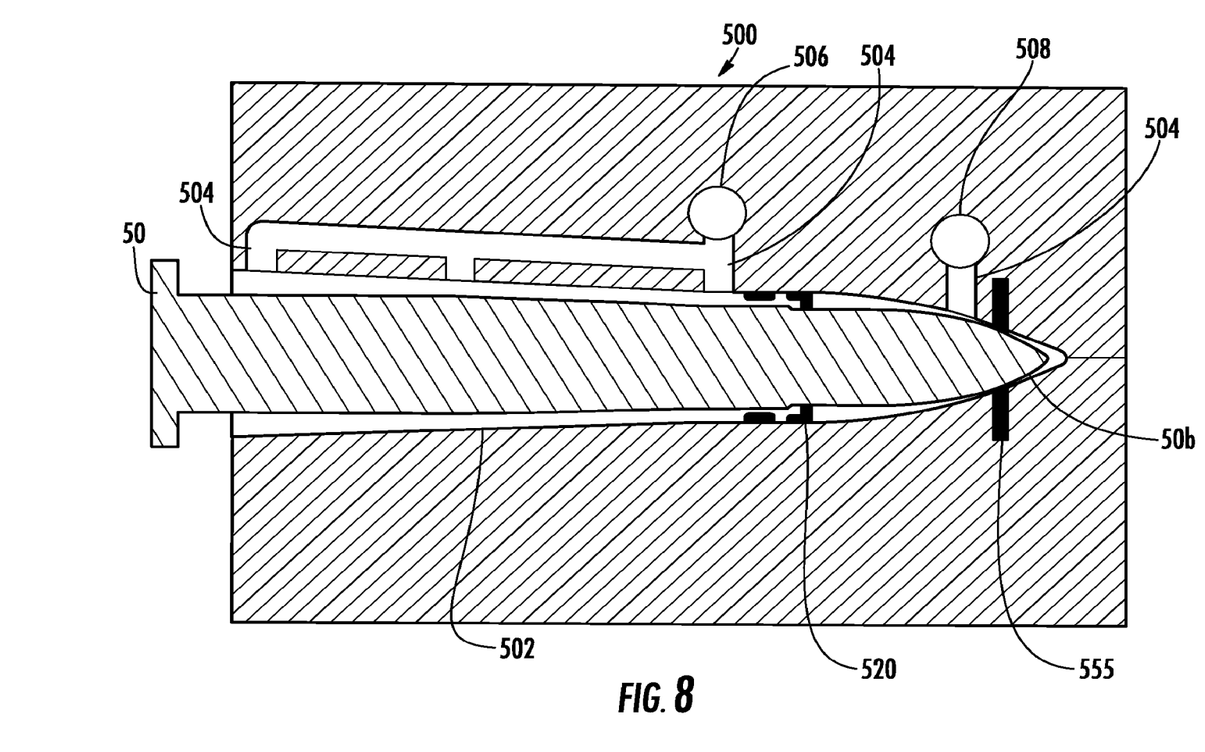
FIGS. 8-10 are cross-sectional views of a mold for use in manufacture of the optical obturator of FIG. 1.

Injection mold 500 includes multiple valve gates 504 through which molten polymer is forced into the mold cavity. Gates 504 serve to create shear in the molten polymer to further decrease viscosity and to aid with material flow in the mold cavity. By including multiple gates 504 in mold 500, mold 500 flow length increases, enabling a larger mold cavity to be completely filled more easily and reducing the incidents of voids forming in the mold cavity. Gates 504 may also be pin point gates or edge gates.

A first material such as, e.g., molten polymer, contained in a first reservoir 506 is injected into mold cavity 502 and the first material flows between the walls of mold cavity 502 and core pin 50. Alternatively, mold material may be introduced through an opening from an external source of the mold material. In this manner, tubular shaft 12 is formed. In addition, mold 500 includes a hot runner system (not shown) that facilitates maintaining the molten polymer at a temperature sufficient to promote high flow of the polymer into and through mold cavity 502. Alternatively, mold 500 may include a cold runner system (not shown) in lieu of a hot runner system (not shown).

Figure 6:
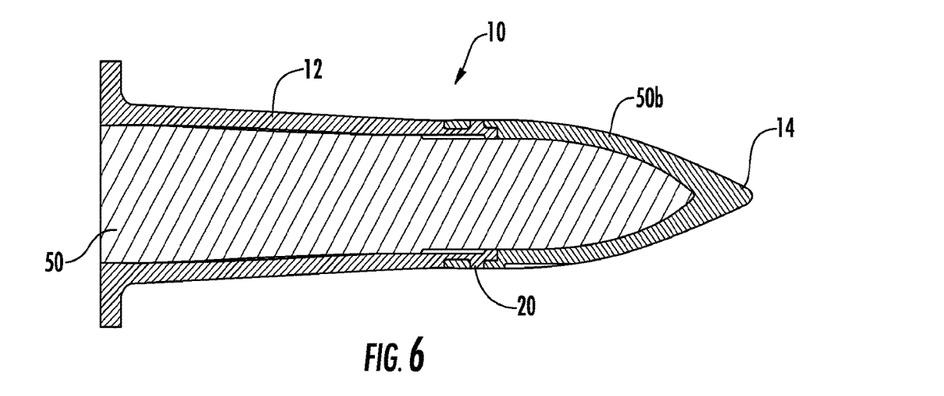
FIG. 6 is a partial, longitudinal cross-sectional view of the optical obturator illustrating a core pin placed within the working channel of the optical obturator.
Figure 7:
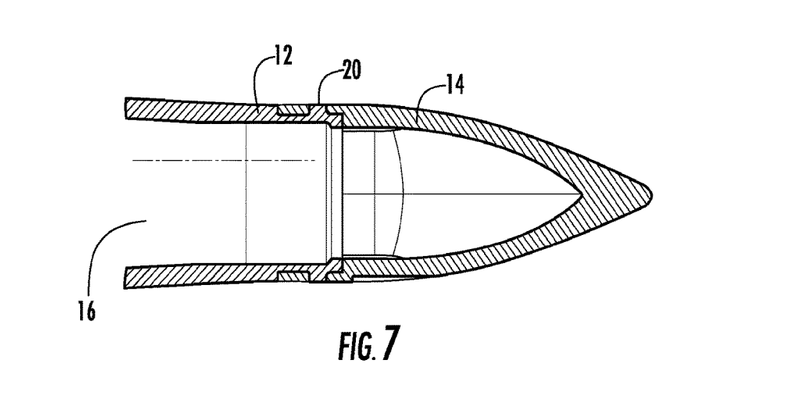
FIG. 7 is a partial, longitudinal cross-sectional view of a distal portion of the optical obturator of FIG. 6 with the core pin removed from the working channel of the optical obturator.
Figure 9:
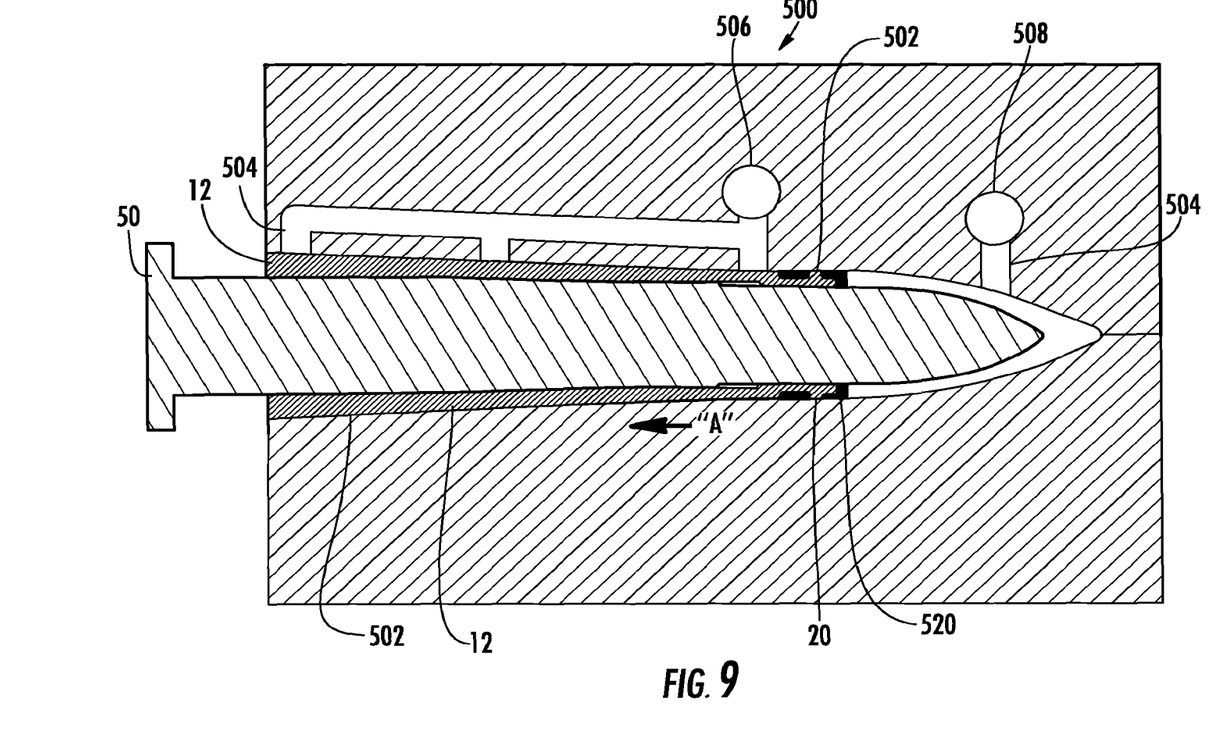

With reference now to FIG. 9, upon forming tubular shaft 12, cantilevered core pin 50 is translated proximally in the direction of arrow "A". Alternatively, the cantilevered core pin 50 may be detached from mold 500 by removing clamp 555. Thereafter, core pin 50 is supported by tubular shaft 12. Moreover, core pin 50 is translated longitudinally, e.g., proximally in the direction of arrow "A", to selectively provide a desired shape and profile of optical tip portion 14. Core pin 50 blocks flow of the second material into tubular shaft 12. In addition, core pin 50 may be moved proximally within tubular shaft 12 to eliminate vacuum created between core pin 50 and tubular shaft 12. For example, as shown in FIGS. 6 and 9, core pin 50 has been shifted proximally with respect to tubular shaft 12. Moreover, portions 520 of mold 500 that define axial retention rib 20 and flow channel 22 of tubular shaft 12 are removed such that optical tip portion 14 may be molded over axial retention rib 20 and flow channel 22.

Figure 10:
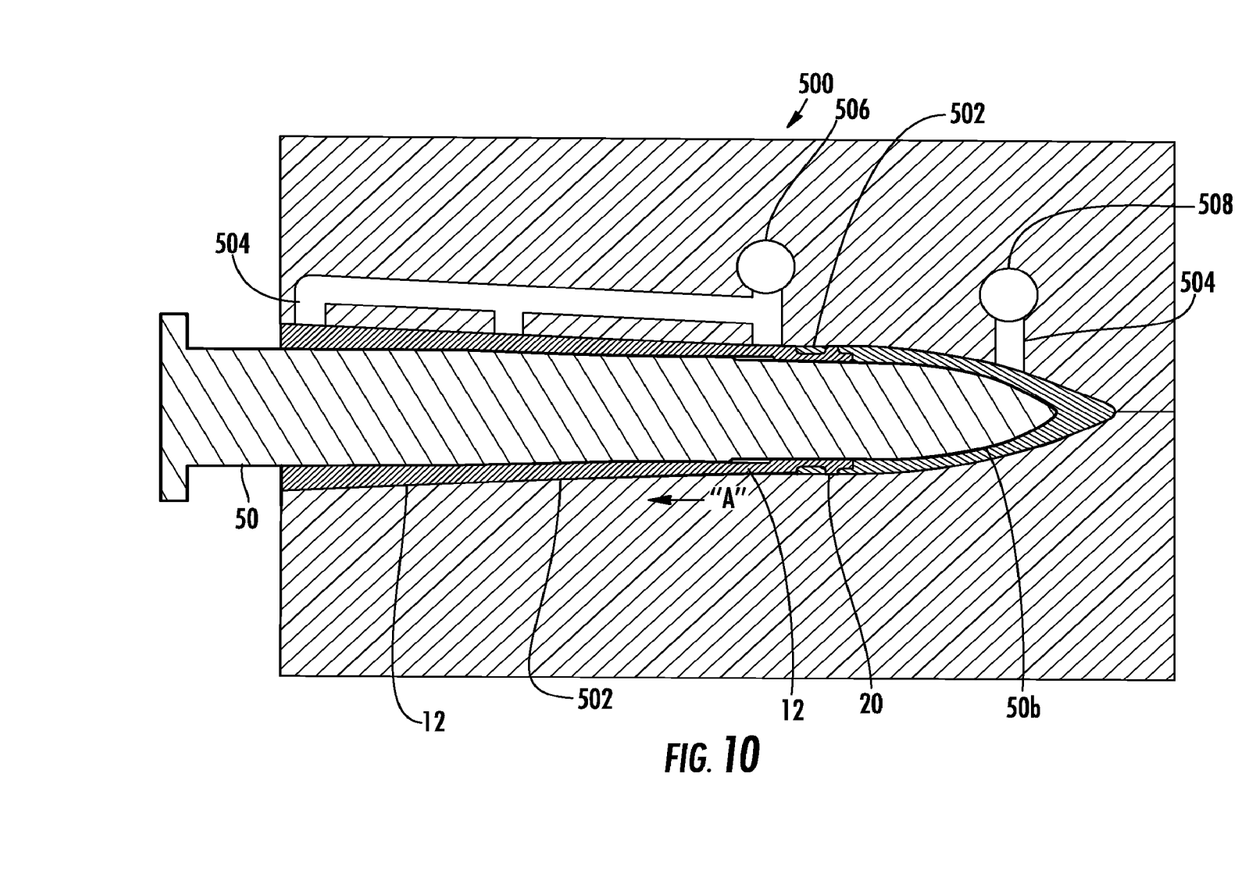

With reference now to FIG. 10, upon determining the desired location of core pin 50 and positioning core pin 50 at the desired location, a second material is injected into mold cavity 502 from a second reservoir 508 to form optical tip portion 14 (FIG. 5). The second material flows between the walls of mold cavity 502 defining the shape and profile of optical tip portion 14 and a distal end 50b of core pin 50. The second material flows through flow channel 22 (FIG. 3) formed on tubular shaft 12 and forms optical tip portion 14 thereon, as shown in FIG. 6. Cooling process of the second material strengthens the bond between distal end of core pin 50 and optical tip portion 14.

Optical obturator 10 including formed tubular shaft 12 and optical tip portion 14 reduces costs of manufacture in comparison with multiple-piece optical obturator, as no secondary assembly operations are required for attaching optical tip portion 14 to tubular shaft 12. Moreover, the cantilevered core pin 50 eliminates the need for the plurality of core pin supports which, in turn, eliminates bores in tubular shaft 12 formed by the core pin supports, and thereby resulting in tubular shaft 12 having hermetically sealed walls. Such a configuration inhibits fluids and tissue from entering working channel 16 of optical obturator 10.

Optical obturator 10 may be disposable after use or may be sterilized for subsequent use. It is envisioned that optical obturator 10 may include a housing (not shown) including an opening and an endoscope retention member adjacent the opening. The scope retention member is adapted to engage the outer surface of the endoscope in a frictional engagement therewith to assist in retaining the relative positioning of the endoscope within optical obturator 10.

The endoscope may be positioned within optical obturator 10 and advanced through an incision and into the body cavity as a unitary construct. During the advancement within tissue, the endoscope permits constant visualization of the neighboring tissue, and thereby providing confirmation upon entering into the body cavity while also minimizing undesired contact or engagement with any underlying organs or other body tissues. Alternatively, the endoscope may be positioned within optical obturator 10 after optical obturator 10 has been advanced into the body cavity.

The use and function of optical obturator 10 will now be discussed. In laparoscopic surgery, the abdominal cavity is insufflated with a suitable biocompatible gas to insufflate the body cavity and lift the body cavity wall away from the internal organs therein.

In operation, an initial incision is made by, e.g., a scalpel. The incision is preferably small, for example, within a range from about 2 mm to about 7 mm. Optionally, a cannula or an access port (not shown) may be utilized. Optical obturator 10 is at least partially introduced within the cannula assembly. The endoscope is inserted through working channel 16 of optical obturator 10 until visualization is attained through optical tip portion 14. The clinician then positions blunt end portion 21 of optical obturator 10 against the body tissue and continuously moves blunt end portion 21 to dissect or separate tissue along a natural tissue plane to gain access to an underlying cavity in a non-traumatic fashion. During penetration of the body tissue the clinician either observes such penetration through an eyepiece, or in instances where a video system is utilized the clinician observes the penetration of the body tissue via any known video monitor.

The clinician may insert obturator assembly 200 and bluntly penetrate the body tissue until reaching thicker tissue, such as muscle. At this point, a blade (not shown) can be deployed to cut through this thick tissue.

Once optical obturator 10 is positioned at the desired location relative to the body cavity, the endoscope may be used to monitor the desired surgical procedure being performed within the cavity. Alternatively, upon penetration into the body cavity, both the endoscope and optical obturator 10 may be removed from the cannula or access port, while leaving the cannula or access port in the body for insertion of desired surgical instrumentation therethrough.

Figure 11:
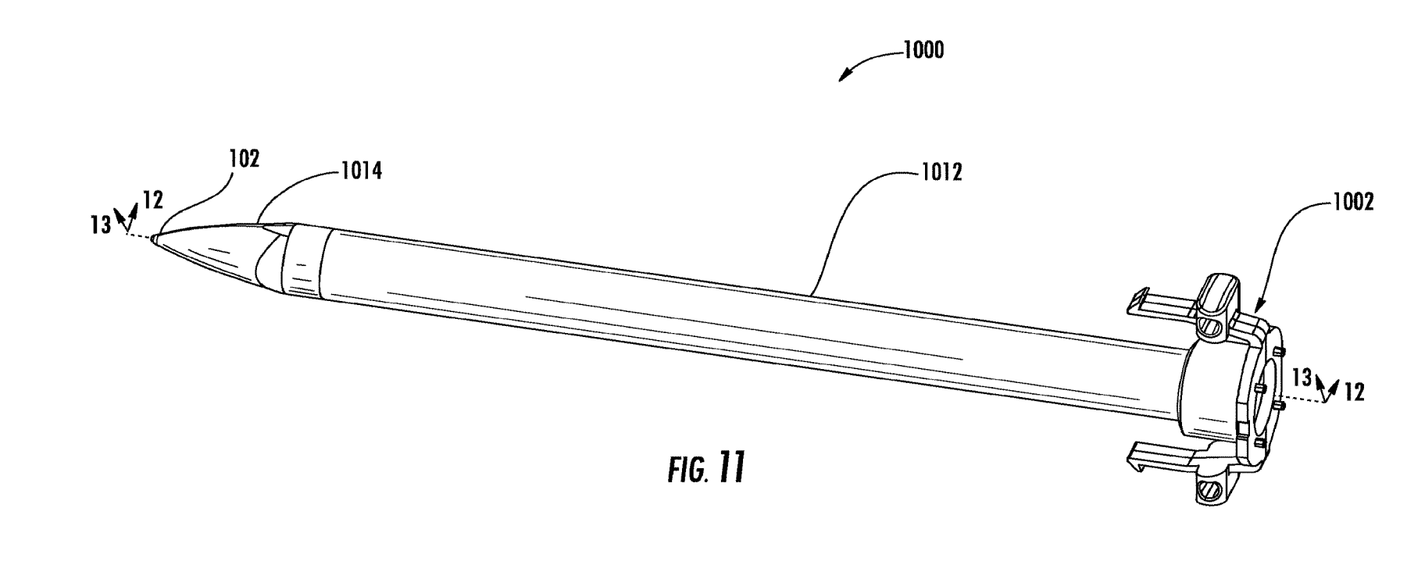
FIG. 11 is a perspective view of an optical obturator in accordance with another embodiment of the present disclosure.

With reference now to FIG. 11, there is illustrated an optical obturator 1000 in accordance with another embodiment of the present disclosure. In the interest of brevity, the present embodiment focuses on the differences between optical obturator 1000 and the previously described optical obturator 10. Optical obturator 1000 may be formed by using a two-shot molding technique as described hereinabove. Optical obturator 1000 includes a latch assembly 1002, a tubular shaft 1012 extending from latch assembly 1002, and an over-molded optical tip portion 1014 extending distally from tubular shaft 1012.

Figure 12:
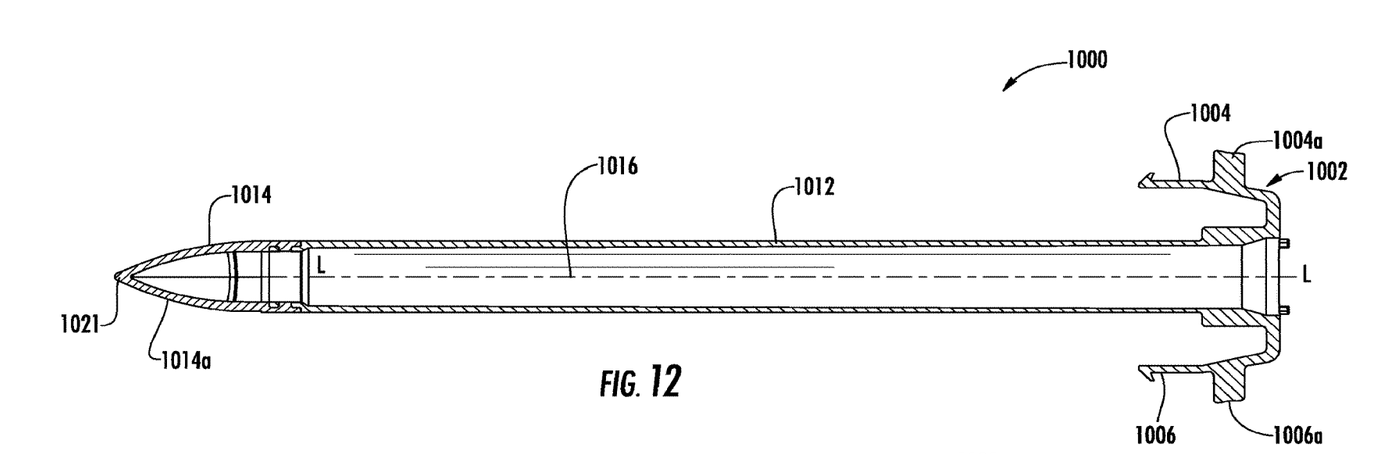
FIG. 12 is a longitudinal cross-sectional view of the optical obturator taken along a section line "12-12" in FIG. 11.
Figure 13:
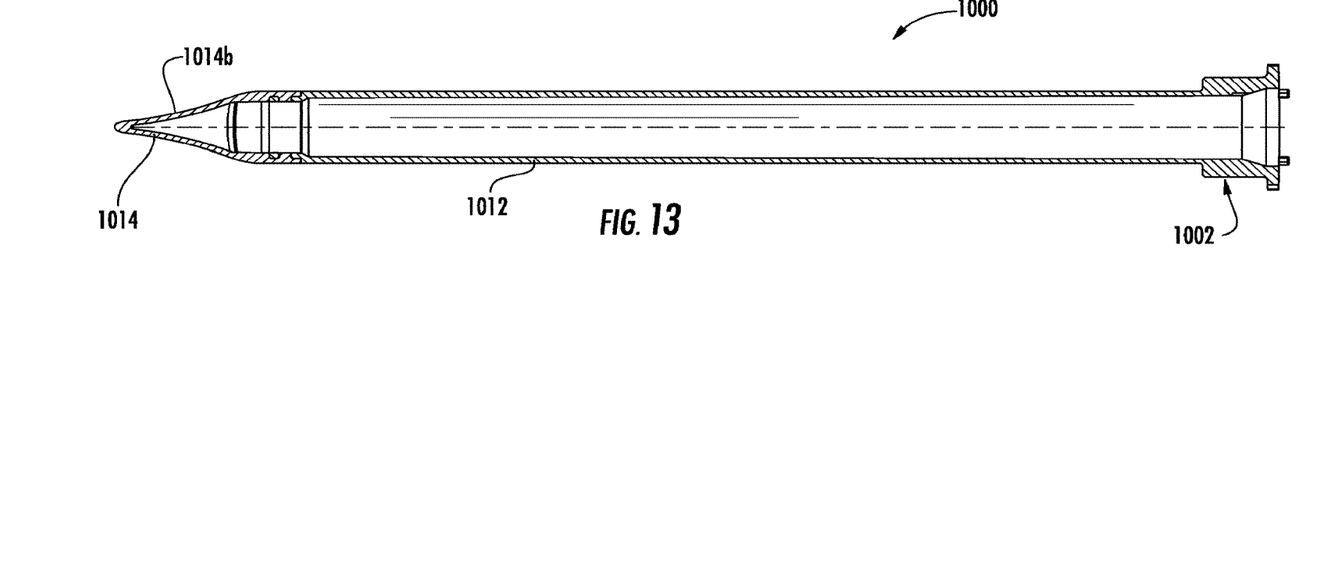
FIG. 13 is a longitudinal cross-sectional view of the optical obturator taken along a section line "13-13" in FIG. 11.

With particular reference to FIGS. 12 and 13, latch assembly 1002 and tubular shaft 1012 may be monolithically formed from, e.g., molten polymer. Latch assembly 1002 includes a pair of diametrically opposed fingers 1004, 1006. Fingers 1004, 1006 are movable radially with respect to a longitudinal axis "L-L" of optical obturator 1000. In particular, each finger 1004, 1006 includes a respective button 1004a, 1006a to facilitate radial movement of fingers 1004, 1006. Tubular shaft 1012 is a substantially hollow structure and defines a working channel 1016 configured and dimensioned to receive an endoscope therein. Working channel 1016 includes a smooth surface finish configured to facilitate sliding insertion and removal of the endoscope towards and away from optical tip portion 1014.

Figure 14:
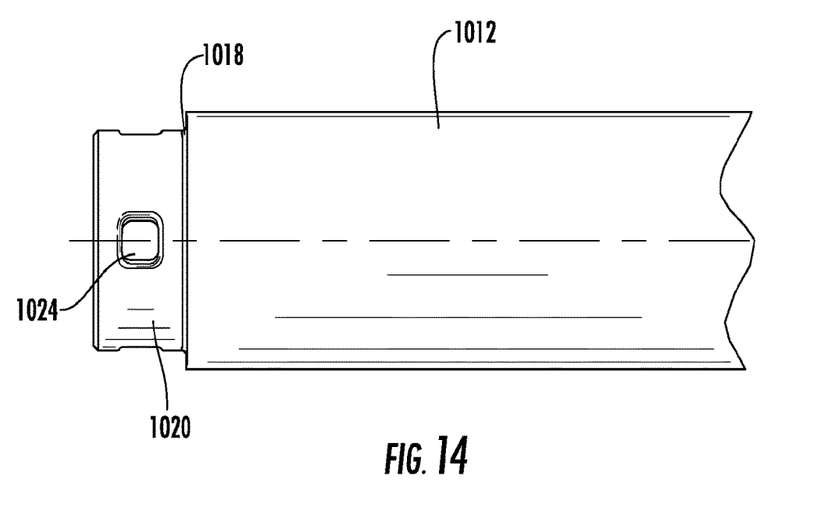
FIG. 14 is a partial side view of a tubular shaft of the optical obturator of FIG. 11, illustrating a distal end portion of the tubular shaft.
Figure 15:
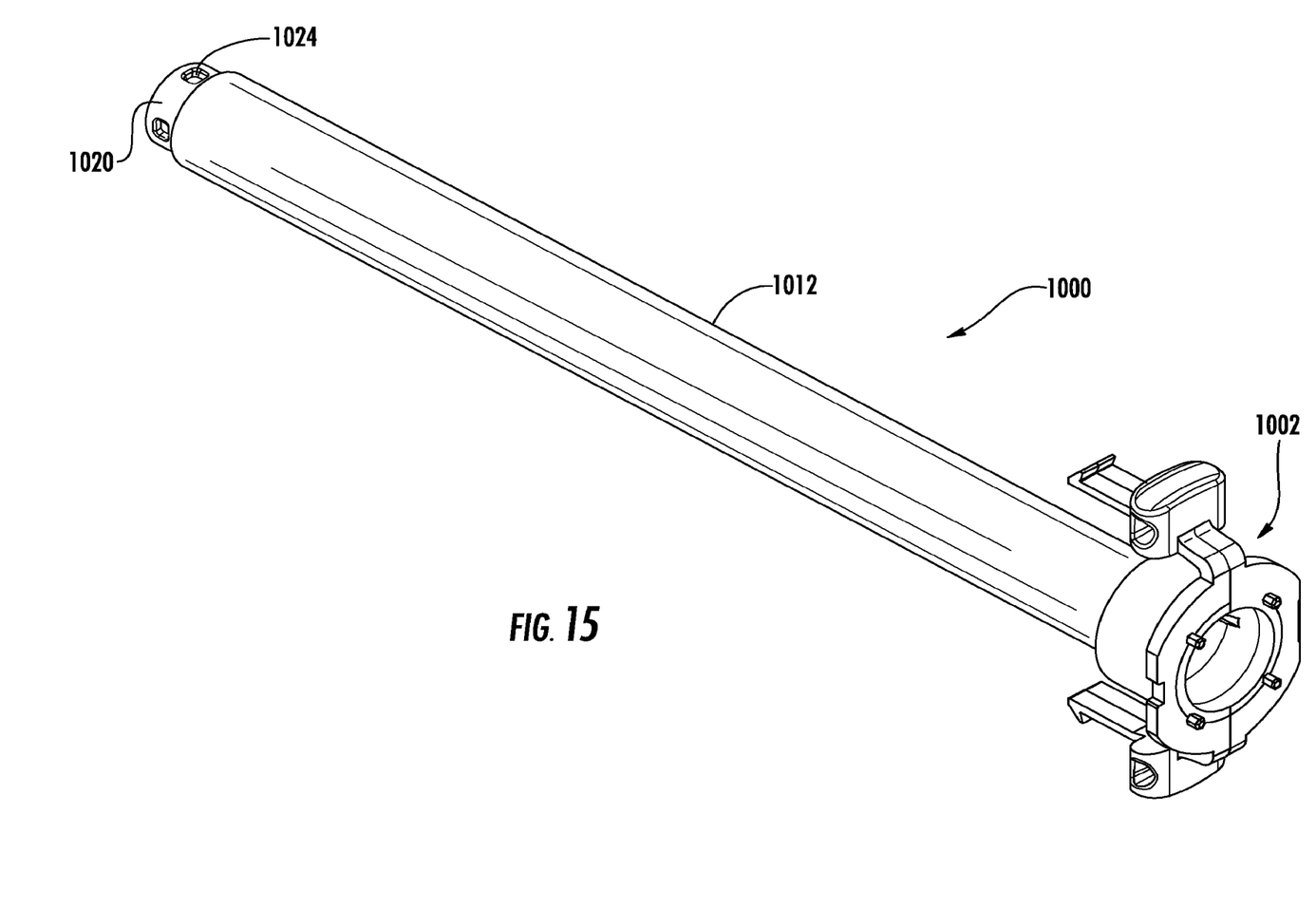
FIG. 15 is a perspective view of the optical obturator of FIG. 11 with the optical tip portion removed.

With reference to FIGS. 14 and 15, a distal portion 1018 of tubular shaft 1012 has an engaging portion 1020 having a smaller diameter than an outer diameter of tubular shaft 1012. Optical tip portion 1014 is formed over or on an outer surface of engaging portion 1020. In this manner, as the molten material of optical tip portion 1014 cools, optical tip portion 1014 shrinks onto engaging portion 1020 of tubular shaft 1012, thereby strengthening the bond therebetween. Such a configuration provides a stronger bond when compared with an optical tip portion that is molded onto, e.g., an inner surface, of tubular shaft 1012. Engaging portion 1020 defines a plurality of circumferentially arranged recesses 1024 to further secure optical tip portion 1014 on engaging portion 1020. Under such a configuration, rotation and axial movement of optical tip portion 1014 relative to engaging portion 1020 is inhibited.

With brief reference back to FIGS. 12 and 13, overmolded optical tip portion 1014 defines a bladeless tip or a blunt end portion 1021 for separating tissue planes and blunt dissection of cavity linings during a surgical procedure. Blunt end portion 1021 permits initial insertion within an opening, e.g., a pre-cut scalpel incision, in tissue and facilitates advancement of tubular shaft 1012 between the tissue layers to gently dissect tissue, without any further cutting or incising of tissue (e.g., atraumatic). In particular, optical tip portion 1014 includes a convex portion 1014a and a concave portion 1014b to facilitate insertion through tissue. Convex portion 1014a and concave portion 1014b may be offset about 90 degrees from each other. After initial insertion and continued distal insertion, tubular shaft 1012 continues to gently enlarge the opening in tissue. Optical tip portion 1014 is made of a transparent material to provide visualization of the tissue tract and the body cavity through the endoscope. Optical tip portion 1014 may be constructed from a number of transparent materials such as, e.g., acrylic, glass, polystyrene, polycarbonate, or amorphous nylon.

Figure 16:
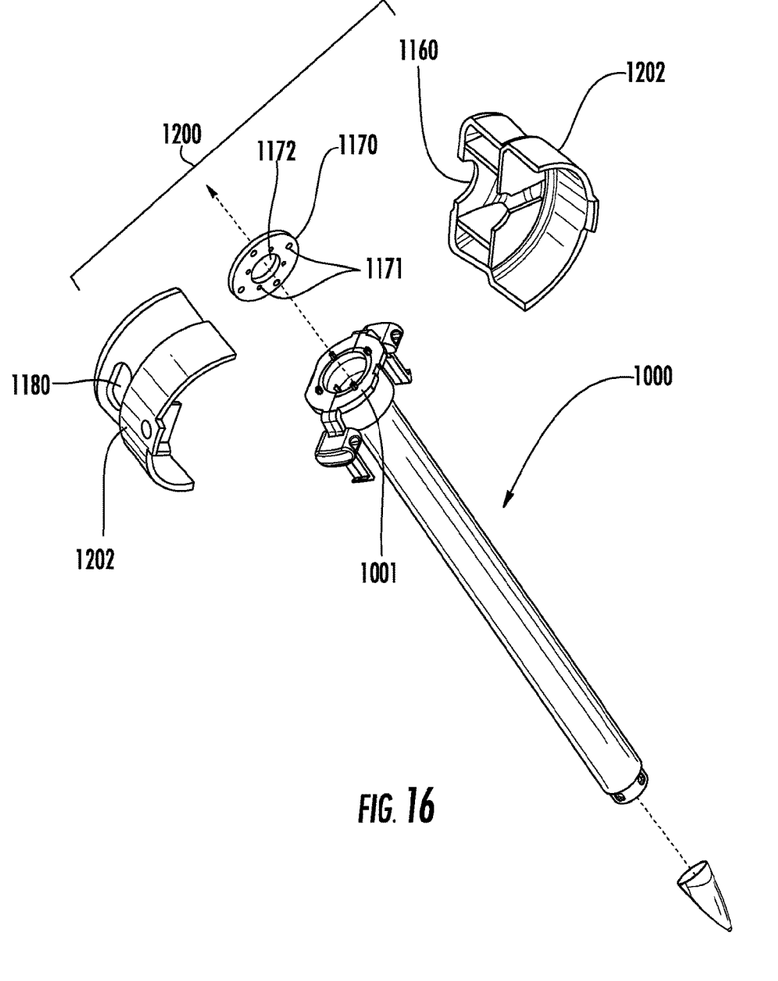
FIG. 16 is an exploded perspective view of an optical obturator assembly with parts separated.

With reference now to FIG. 16, optical obturator 1000 may further include an obturator housing assembly 1200. Obturator housing assembly 1200 includes a housing 1202 configured to be mechanically coupled with a housing of a cannula assembly (not shown). Further details of the cannula assembly are disclosed in U.S. patent application Ser. No. 13/887,420, filed May 6, 2013, and Ser. No. 13/861,428, filed Apr. 12, 2013, the entire contents of each of which are incorporated by reference herein. Housing 1202 defines a pair of openings 1180 and an aperture 1160. Openings 1180 diametrically oppose each other. Each opening 1180 is configured to receive respective one of the pair of buttons 1004a, 1006a (FIG. 12) of latch assembly 1002. Obturator housing assembly 1200 further includes a scope retention member 1170 adjacent aperture 1160. Scope retention member 1170 may be fabricated from an elastomeric material. Scope retention member 1170 defines a plurality of openings 1171. Each opening 1171 is configured to receive respective one of a plurality of protrusions 1001 of latch assembly 1002 to secure scope retention member 1170 to optical obturator 1000. Scope retention member 1170 defines a central opening 1172 for receiving the endoscope and includes four radial slits 1174 extending outwardly from central opening 1172. Radial slits 1174 permit flexure of scope retention member 1170 and enlargement of the central opening 1172 upon insertion of the endoscope. The operation of optical obturator 1000 is substantially identical to that of optical obturator 100 described hereinabove, and thus will not be described.

It will be understood that various modifications and changes in form and detail may be made to the embodiments of the present disclosure without departing from the spirit and scope of the invention. For example, optical obturator 10 may incorporate its own illumination and optical devices or systems. For example, optical obturator 10 may include illumination means and image transmitting means each extending in a general longitudinal direction. Illumination means is configured to transfer illuminating light to the operative site. Illumination means may include fiber optics or a liquid light transferring medium. Illumination means may include a bundle of fiber optic elements or lenses which transfer an optical image for viewing by the clinician.

Therefore, the above description should not be construed as limiting the invention but merely as exemplifications of preferred embodiments thereof. Those skilled in the art will envision other modifications within the scope and spirit of the present invention as defined by the claims appended hereto. Having thus described the invention with the details and particularity required by the patent laws, what is claimed and desired protected is set forth in the appended claims.

What is claimed is:

1. A method of manufacturing an optical obturator including a tubular shaft and an optical tip formed with the tubular shaft, the optical obturator defining a lumen configured and dimensioned to receive an optical instrument for receiving an image of tissue, the method comprising:
    providing an injection mold including a mold cavity defining an outer surface of the optical obturator and a core pin centrally positioned within the mold cavity, the core pin defining an inner surface of the optical obturator;
    injecting a first material between the core pin and the mold cavity to form the tubular shaft;
    translating the core pin proximally within the tubular shaft prior to injecting a second material;
    injecting the second material between a distal portion of the core pin and a distal portion of the mold cavity to form the optical tip.

2. The method according to claim 1, wherein providing the injection mold including the mold cavity defining the outer surface of the optical obturator and the core pin centrally positioned within the mold cavity includes providing the core pin having an end portion cantilevered to the injection mold.

3. The method according to claim 1, further comprising detaching the core pin and positioning the core pin within the tubular shaft such that the core pin is centrally supported by the tubular shaft.

4. The method according to claim 1, wherein injecting the second material includes injecting a high-flow polycarbonate material.

5. The method according to claim 1, wherein injecting the second material includes injecting a transparent, molten polymeric material having high-flow properties such that the polymeric material flows between a surface of the mold cavity and the core pin.

6. The method according to claim 1, wherein providing the injection mold including the mold cavity defining the outer surface of the optical obturator and the core pin centrally positioned within the mold cavity includes providing the core pin detachably supported with the injection mold.

7. The method according to claim 1, wherein injecting the second material between the distal portion of the core pin and the distal portion of the mold cavity to form the optical tip includes injecting the second material between the distal portion of the core pin and the distal portion of the mold cavity to form the optical tip including a blunt end portion configured for separation of tissue planes and blunt dissection of cavity linings.

8. The method according to claim 1, wherein providing the injection mold including the mold cavity defining the outer surface of the optical obturator and the core pin centrally positioned within the mold cavity includes providing the core pin having a varying diameter.

9. The method according to claim 1, further comprising curing the second material such that the second material encapsulates a distal portion of the tubular shaft.

10. The method according to claim 1, wherein injecting the first material between the core pin and the mold cavity to form the tubular shaft further includes forming a latch assembly.

11. The method according to claim 1, wherein translating the core pin proximally within the tubular shaft includes eliminating vacuum created between the tubular shaft and the core pin.

* * * * *